(12) United States Patent
Jeong et al.

(10) Patent No.: US 8,324,365 B2
(45) Date of Patent: Dec. 4, 2012

(54) CONJUGATE FOR GENE TRANSFER COMPRISING OLIGONUCLEOTIDE AND HYDROPHILIC POLYMER, POLYELECTROLYTE COMPLEX MICELLES FORMED FROM THE CONJUGATE, AND METHODS FOR PREPARATION THEREOF

(75) Inventors: Ji Hoon Jeong, Seoul (KR); Tae Gwan Park, Daejeon (KR)

(73) Assignees: Korea Advanced Institute of Science and Technology, Daejeon (KR); Bioneer Corporation, Daejeon (KR); Samyang Corporation, Seoul (KR)

( * ) Notice: Subject to any disclaimer, the term of this patent is extended or adjusted under 35 U.S.C. 154(b) by 181 days.

(21) Appl. No.: 10/551,466

(22) PCT Filed: Apr. 3, 2003

(86) PCT No.: PCT/KR03/00665
§ 371 (c)(1),
(2), (4) Date: Aug. 7, 2006

(87) PCT Pub. No.: WO2004/087931
PCT Pub. Date: Oct. 14, 2004

(65) Prior Publication Data
US 2007/0041932 A1    Feb. 22, 2007

(51) Int. Cl.
*C07H 21/04* (2006.01)
(52) U.S. Cl. .................................................. 536/24.5
(58) Field of Classification Search .............. 536/24.5
See application file for complete search history.

(56) References Cited

U.S. PATENT DOCUMENTS

| | | | |
|---|---|---|---|
| 4,904,582 A * | 2/1990 | Tullis ................................ | 435/6 |
| 5,543,507 A * | 8/1996 | Cook et al. .................... | 536/23.1 |
| 5,714,166 A | 2/1998 | Tomalia et al. | |
| 5,717,083 A * | 2/1998 | Cook et al. .................... | 536/23.1 |
| 6,221,959 B1 | 4/2001 | Kabanov et al. | |
| 6,521,456 B1 | 2/2003 | Siebenkotten et al. | |
| 7,737,108 B1 * | 6/2010 | Hoffman et al. ................... | 514/2 |
| 7,777,024 B2 * | 8/2010 | Miculka et al. .............. | 536/25.6 |
| 2001/0005717 A1 | 6/2001 | Wagner et al. | |
| 2003/0130186 A1 * | 7/2003 | Vargeese et al. ................ | 514/12 |
| 2004/0167090 A1 | 8/2004 | Monahan et al. | |
| 2004/0266707 A1 | 12/2004 | Leake et al. | |

FOREIGN PATENT DOCUMENTS

| | | |
|---|---|---|
| CA | 2 619 533 A1 | 2/2007 |
| EP | 1 801 210 A1 | 6/2007 |
| WO | WO 02/43769 | 6/2002 |
| WO | WO 2004/009769 A2 | 1/2004 |
| WO | WO 2004/044141 A2 | 5/2004 |
| WO | WO 2004/076630 A2 | 9/2004 |
| WO | WO 2004/087931 A1 | 10/2004 |

OTHER PUBLICATIONS http://www.newton.dep.anl.gov/askasci/mole00/mole00415.htm—accessed Dec. 27, 2007.*

Raschella, et al. (1992) Inhibition of proliferation by c-myb antisense RNA and oligodeoxynucleotides in transformed neuroectodermal cell lines. Cancer Research, v.52:4221-4226.*
Goodchild (1990) Conjugates of Oligonucleotides and Modified Oligonucleotides: A Review of Their Syhthesis and Properties. Bioconjugate Chemistry, v.1(3):165-187.*
Bennett, et al. (1994) Inhibition of Vascular Smooth Muscle Cell Proliferation In Vitro and in Vivo by C-myc Antisense Oligodeoxynucleotides. J. Clin. Invest., v.93:820-828.*
Jeong, et al. (2001) Novel Intracellular Delivery System of Antisense Oligonucleotide by Self-Assembled Hybrid Micelles Composed of DNA/PEG Conjugate and Cationic Fusogenic Peptide. Bioconjugate Chemistry, v.14:473-9.*
Agrawal et al., (1988) Oligodeoxynucleoside Phosphoramidates and Phosphorothioates as Inhibitors of Human Immunodeficiency Virus. Proc. Natl. Acad. Sci. v.85:7079-7083.*
Matysaik et al. Nucleosides & Nucleotides 16(5&6), 855-861, 1997.*
Fisher et al., "Intracellular disposition and metabolism of fluorescently-labeled unmodified and modified oligonucleotides microinjected into mammalian cells," *Nucleic Acids Res.* 21:3857-3865, Oxford University Press (1993).
Kataoka et al., "Spontaneous formation of polyion complex micelles with narrow distribution from antisense oligonucleotide and cationic block copolymer in physiological saline," *Macromolecules* 29:8556-8557, American Chemical Society (1996).
Milligan et al., "Current concepts in antisense drug design," *J. Med. Chem.* 36:1923-1937, American Chemical Society (1993).
Bonora, "Polymer-conjugated Bioactive Oligonucleotides," *Journal of Bioactive and Compatible Polymers* 17:375-389 (Sep. 2002) Sage Publications. Healy et al., "Pharmacokinetics and Biodistribution of Novel Aptamer Compositions," *Pharmaceutical Research* 21:2234-2246 (2004) Springer Science+Business Media, Inc.
Jeong et al., "Novel Intracellular Delivery System of Antisense Oligonucleotide by Self-Assembled Hybrid Micelles Composed of DNA/PEG Conjugate and Cationic Fusogenic Peptide," *Bioconjugate Chem.* 14:473-479 (Mar. 2003) American Chemical Society.

(Continued)

Primary Examiner — Brian Whiteman
(74) Attorney, Agent, or Firm — Sterne, Kessler, Goldstein & Fox PLLC (57) ABSTRACT

Disclosed is a conjugate for gene transfer, which is capable of being used for treatment of incurable diseases, comprising an oligonucleotide intended to be transferred into target cells and a hydrophilic polymer, wherein an end of the oligonucleotide is covalently conjugated to the hydrophilic polymer. Also, the present invention discloses polyelectrolyte complex micelles formed from such a conjugate and a cationic polymer or cationic peptide. Such polyelectrolyte complex micelles can effectively transfer oligonucleotides as therapeutic agents into target cells, making it possible to obtain desired activities of the delivered oligonucleotides in target cells even when the micelles are clinically applied at a relatively low concentration. Therefore, the conjugate and the polyelectrolyte complex micelle are very useful in basic life science research and the medical field.

13 Claims, 8 Drawing Sheets

OTHER PUBLICATIONS

Jeong et al., "A New Antisense Oligonucleotide Delivery System Based on Self-Assembled ODN-PEG Hybrid Conjugate Micelles," *Journal of Controlled Release 93*:183-191 (Dec. 2003) Elsevier B.V.

Jones et al., "Conjugates of Double-Stranded Oligonucleotides with Poly(ethylene glycol) and Keyhole Limpet Hemocyanin: A Model for Treating Systemic Lupus Erythematosus," *Bioconjugate Chem. 5*:390-399 (1994) American Chemical Society.

Kawaguchi et al., "Stability, Specific Binding Activity, and Plasma Concentration in Mice of an Oligodeoxynucleotide Modified at 5'-Terminal with Poly(ethylene glycol)," *Biol. Pharm. Bull. 18*:474-476 (1995) Pharmaceutical Society of Japan.

Kim et al., "Target-Specific Gene Silencing by siRNA Plasmid DNA Complexed with Folate-Modified Poly(ethylenimine)," *Journal of Controlled Release 104*:223-232 (2005) Elsevier B.V.

Kim et al., "PEG conjugated VEGF siRNA for anti-angiogenic gene therapy," *Journal of Controlled Release 116*:123-129 (2006) Elsevier B.V.

Lee et al., "Intracellular siRNA Delivery System Using Polyelectrolyte Complex Micelles Prepared from VEGF siRNA-PEG Conjugate and Cationic Fusogenic Peptide," *Biochemical and Biophysical Research Communications 357*:511-516 (2007) Elsevier Inc.

Oishi et al., "Smart Polyion Complex Micelles for Targeted Intracellular Delivery of PEGylated Antisense Oligonucleotides Containing Acid-Labile Linkages," *ChemBioChem 6*:718-725 (2005) Wiley-VCH Verlag GmbH & Co. Weinheim.

Oishi et al., "Lactosylated Poly(ethylene glycol)—siRNA Conjugate through Acid-Labile β-Thiopropionate Linkage to Construct pH-Sensitive Polyion Complex Micelles Achieving Enhanced Gene Silencing in Hepatoma Cells," *J. Am. Chem. Soc. 127*:1624-1625 (2005) American Chemical Society.

Bertrand, J-R., et al., "Comparison of antisense oligonucleotides and siRNAs in cell culture and in vivo," *Biochem. Biophys. Res. Commun. 296*:1000-1004, Elsevier Science, United States (Aug. 2002).

Heyes, J., et al., "Cationic lipid saturation influences intracellular delivery of encapsulated nucleic acids," *Journal of Controlled Release 107*:276-287, Elsevier B.V., Netherlands (2005).

*Trans*IT-TKO® siRNA Transfection Reagent, Lit. # FAQ003 Rev. Jan. 4, 2006[online]. Mirus, Apr. 1, 2006 (Jan. 4, 2006) [retrieved on Jun. 20, 2011]. Retrieved from Internet: <URL: http://www.mirusbio.com/assets/cms_files/faqs/FAQ003.pdf.>.

\* cited by examiner

//  CONJUGATE FOR GENE TRANSFER COMPRISING OLIGONUCLEOTIDE AND HYDROPHILIC POLYMER, POLYELECTROLYTE COMPLEX MICELLES FORMED FROM THE CONJUGATE, AND METHODS FOR PREPARATION THEREOF

TECHNICAL FIELD

The present invention relates to a conjugate comprising an oligonucleotide and a hydrophilic polymer, which is capable of being used for treatment of incurable diseases, and polyelectrolyte complex micelles formed from interaction between such a conjugate and a cationic polymer or cationic peptide, where formation of the micelle is driven by ionic interaction between the two components. Also, the present invention is concerned with methods of preparing such a conjugate and such polyelectrolyte complex micelles.

BACKGROUND ART

Safe and effective gene transfer techniques for gene therapy have been studied for a long time, resulting in development of various gene transfer vehicles and gene delivery systems. In particular, vectors based on adenoviruses and retroviruses, and nonviral vectors using liposomes, cationic lipids and cationic polymers have been developed as gene transfer vehicles. However, there are significant problems when viruses are used as vehicles for transfer of therapeutic genes into target cells, as follows. The transferred genes can negatively affect function of host genes after integration into host chromosome, and there is no evidence for the transferred gene do not activate oncogenes. In addition, if viral genes are continuously expressed even at a small amount, autoimmune response may be induced. Moreover, if a variant of the virus used as a gene transfer vehicle emerges in a host, the host may become infected with the variant, and the host immune system may not effectively protect itself from the variant. For these reasons, rather than the vectors based on viruses, gene delivery systems using liposomes, or cationic lipids or polymers are preferred, and related studies aim to improve the alternative systems. Such nonviral gene transfer vectors are less effective than the viral vectors, but are advantageous in terms of safety due to mild side effects and being economical due to low cost production, thereby allowing industrial production of improved nonviral vectors.

A micelle is a single layer sphere, which is spontaneously formed by self-assembly of molecules having both hydrophilic and hydrophobic groups in an aqueous environment to maximize thermodynamic stability. Block copolymers are able to form self-assembled micelles in an aqueous solution. The inside of the micelles is hydrophobic and thus can easily entrap water-insoluble drugs, and the surface of the micelles is hydrophilic and thus facilitates solubilization of the water-insoluble drugs, thereby allowing its use for drug delivery. Micelles having the hydrophobic core and the hydrophilic shell are stabilized in an aqueous environment by hydrophobic interaction, or ionic interaction between polyelectrolytes having opposite charges. A polyethylene glycol (PEG)-conjugated polyelectrolyte spontaneously associates with another polyelectrolyte having an opposite charge to form complexes having a micellar structure, which are called polyelectrolyte complex micelles (Kataoka, K., Togawa, H., Harada, A., Yasugi, K., Matsumoto, T., Katayoshe, S., Macromolecules. 29, 8556-8557, 1996). The polyelectrolyte complex micelles are more attractive than other drug delivery systems, such as microspheres or nanoparticles, due to their properties of having a very small size and a very uniform size distribution, and being a self-associated structure, thereby facilitating quality control and reproduction of pharmaceutical preparations.

Polymers used for drug delivery to a target site of the body should be biocompatible. A representative example of such biocompatible polymers is polyethylene glycol (PEG). PEG, which has gained approval for in vivo use from the Food and Drug Administration (FDA) of USA, has been utilized for a long time in a broad range of applications from improvement of protein characteristics and surface modification of polymers used in drug delivery systems to gene transfer. PEG, which is one of the most widely used biocompatible polymers, has excellent water solubility, and low toxicity and immunogenicity. In addition, PEG can strongly inhibit absorption of proteins to the polymers used in drug delivery by modifying the surface properties of the polymers.

On the other hand, oligonucleotides have been used in treating diseases in humans and animals. For example, some antisense oligonucleotides are known to regulate expression of genes related to viral and fungal infections and metabolic diseases. Typically, antisense means a complementary oligonucleotide to a target nucleic acid sequence, where the oligonucleotide can hybridize to the target sequence. When a target gene is determined, a nucleic acid sequence sufficiently complementary, which is specifically hybridizing to a part of the target gene, is selected to accomplish desired inhibition of the target gene. However, antisense oligonucleotides are problematic with respect to their delivery to target cells, their lifetime in target cells, and their delivery efficiency to target cells through the plasma membrane. Since the backbone of the linear oligonucleotide is composed of repeating sugar and phosphate residues held together by phosphodiester bonds, most oligonucleotides are easily degraded in cells, especially by nuclease attack. In addition, owing to their short half-life of about 20 min, oligonucleotides should be continuously delivered to target cells at a proper concentration to achieve their therapeutic effect. Oligonucleases sensitive to nuclease digestion can have improved stability by introduction of phosphothioate groups (Milligan, J. F., Mateucci, M. D., Martin, J. C., J. Med. Chem. 36, 1923-1937, 1993), or 2-O-allyl groups (Fisher, T. L., Terhorst, T., Cao, X., Wagner, R. W., Nucleic Acid Res. 21, 3857-3865, 1993). However, techniques related to effective penetration of oligonucleotides through plasma membrane are still under development.

At present, antisense oligonucleotides are delivered to target cells by microinjection, a gene transfer system using cationic polymers or lipids, or a method of directly dispersing oligonucleotides in culture media However, other methods except for the microinjection method do not have high efficiency in delivery of antisense oligonucleotides to target cells.

DISCLOSURE OF THE INVENTION

It is therefore an object of the present invention to provide a conjugate for gene transfer, comprising an oligonucleotide having a functional group at its 5' or 3' end and a hydrophilic polymer having good biocompatibility, which is held together by a cleavable or non-cleavable bond, and a method of preparing such a conjugate.

It is another object of the present invention to provide polyelectrolyte complex micelles formed from the aforementioned conjugate for gene and a cationic polymer or cationic peptide, which is a self-assembled structure driven by interaction between the two components, and a method of preparing such a polyelectrolyte complex micelle.

Further, the present invention aims to improve intracellular delivery efficiency of an antisense oligonucleotide provided as a therapeutic agent for gene therapy, using the aforementioned polyelectrolyte complex micelles.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARING OUT THE INVENTION

In accordance with an aspect of the present invention, there is provided a conjugate for gene transfer, comprising an oligonucleotide intended to be delivered to target cells and a hydrophilic polymer, where the 5' or 3' end of the oligonucleotide is covalently linked to the hydrophilic polymer.

In accordance with another aspect of the present invention, there is provided a gene delivery system using micelles capable of effectively transferring oligonucleotides, such as antisense oligonucleotides useful for experimental purposes and in the medical field, to target cells.

The oligonucleotides include nucleotide sequences useful for gene therapy, which are exemplified by medically valuable antisense oligonucleotides and peptide nucleic acids (PNAs). Also, the main chain of an oligonucleotide useful in the present invention includes phosphodiester bond, phosphorothioate linkage, phosphoroamidate linkage, or amide bond.

Preferably, the oligonucleotide has a molecular weight ranging from 1,000 to 50,000 daltons, where oligonucleotides having a molecular weight of this range can specifically bind to DNA or RNA molecules. Examples of the oligonucleotide satisfying such a condition may include antisense oligonucleotides which selectively hybridize with c-myc, c-myb, c-fos, c-raf, c-ras c-src or c-jun genes, and a portion or entire nucleotide sequence of each of the genes.

In accordance with the present invention, the oligonucleotide is linked to a hydrophilic polymer via covalent bonding to form a conjugate. The conjugate is spontaneously associated with a cationic polymer to form micelles, where the self-association is driven by hydrophobic and ionic interactions. Because of being a component of the micelles, the hydrophilic polymer should be selected from biocompatible polymers being non-toxic and non-immunogenic. Preferably, the hydrophilic polymer is selected from non-ionic polymers having a molecular weight of over 500. Examples of the hydrophilic polymer include polyethylene glycol (PEG), polyvinylpyrrolidone, and polyoxazoline. PEG is most preferable owing to its characteristics of being non-toxic, and having excellent effectiveness in improvement of protein characteristics and surface modification of polymers.

Linkage between the hydrophilic polymer and the oligonucleotide of the conjugate may be achieved by one selected from the group consisting of non-cleavable linkages including amide bond and carbamate linkage, acid-cleavable linkages including hydrazone bond, phosphoroamidate linkage and acetal bond, disulfide bond, ester bond, anhydride-cleavable linkage, and enzyme-cleavable linkage.

The conjugate for gene transfer may be prepared according to a process comprising the following two steps:

(1) activating an end (for example, 5' or 3' end) of an oligonucleotide; and (2) covalently linking a hydrophilic polymer to the end of the oligonucleotide, wherein, chemical compounds useful in the activation of an end of the oligonucleotide are exemplified by 1-ethyl-3,3-dimethylaminopropyl carbodiimide (EDAC), imidazole, N-hydroxsuccinimide (NHS) and dicyclohexylcarbodiimide (DCC), HOBt (1-hydroxybenzotriazole), p-nitrophenylchloroformate, carbonyldiimidazole (CDI), and N,N'-disuccinimidyl carbonate (DSC).

Figure 1:
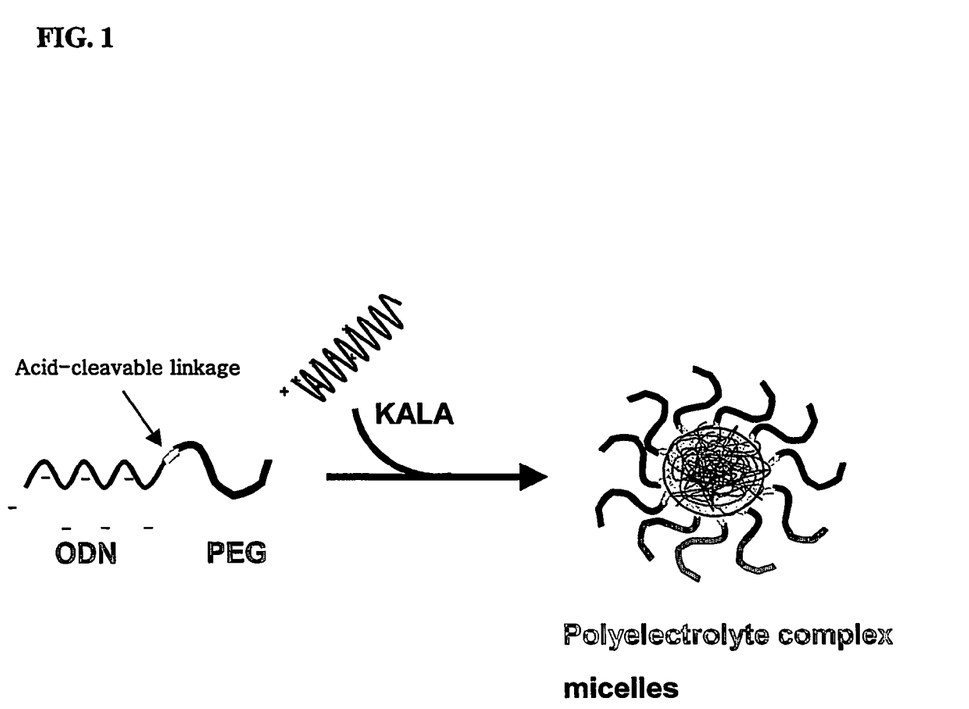
FIG. 1 is a schematic view of a structure of a polyelectrolyte complex micelle according to the present invention.

The present invention provides polyelectrolyte complex micelles formed from the conjugate and a cationic peptide or cationic polymer, where formation of the micelle is driven by ionic interaction. FIG. 1 schematically illustrates a process of preparing a polyelectrolyte complex micelle, in which acid-cleavable linkage-containing oligonucleotide (ODN)-PEG conjugates are self-assembled with a cationic peptide, KALA, to form polyelectrolyte complex micelles.

Examples of the cationic peptides include KALA and protamine, and examples of the cationic polymers include polyethylenimine, polyamidoamine, polylysine, diethylaminoethyldextran, poly(dimethylaminoethyl methylacrylate), and derivates thereof.

The present invention will be explained in more detail with reference to the following examples in conjunction with the accompanying drawings. However, the following examples are provided only to illustrate the present invention, and the present invention is not limited to them.

EXAMPLE 1

Figure 2:
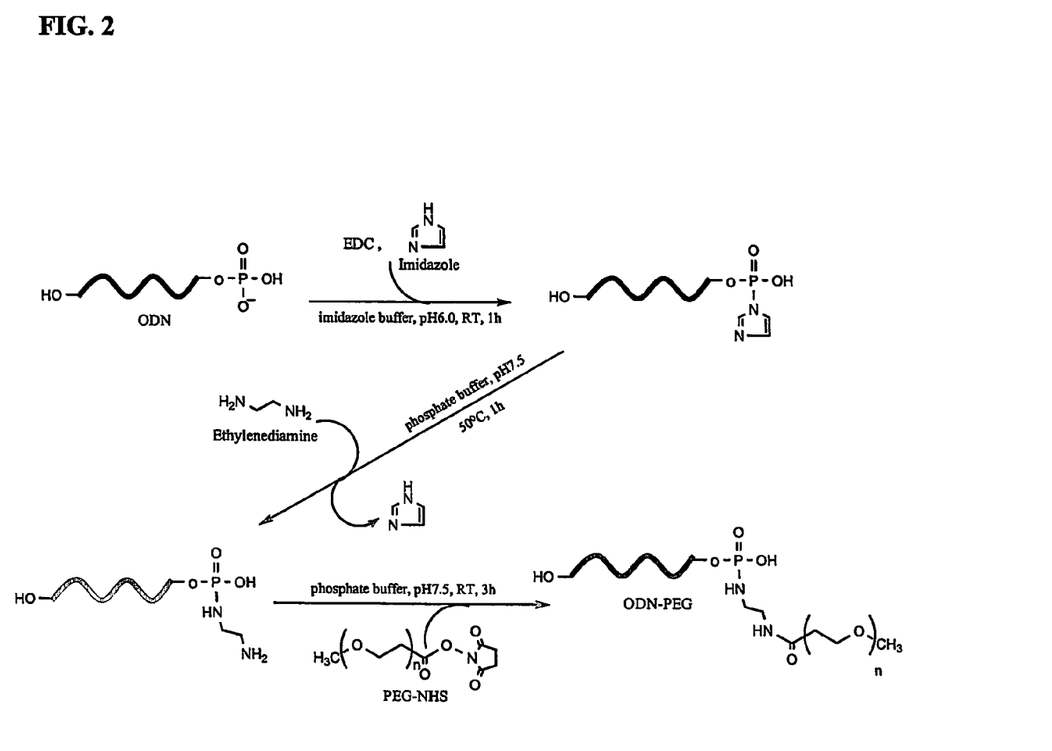
FIG. 2 is a schematic view of a process of conjugating an oligonucleotide having an acid-cleavable bond with a hydrophilic polymer, polyethylene glycol (PEG), according to the present invention.

Synthesis of Oligonucleotide-Peg Conjugate Having Acid-Cleavable Linkage (see FIG. 2)

In this test, a c-myb antisense oligonucleotide was used. After introducing a phosphate group to its 5' end, the antisense oligonucleotide was activated by 1-ethyl-3,3-dimethylaminopropyl carbodiimide (EDAC) and imidazole to generate an oligonucleotide-phosphoimidazole intermediate, as follows. First, to form an active ODN-phosphoimidazolide intermediate, ODN (1 mg, 180 nmol) and EDC (3.5 mg, 18 µmol) was dissolved in 0.5 ml of 0.1 M imidazole (pH 6.0). The reaction mixture was incubated for 1 h at room temperature. The ODN having an imidazolide group at its 5' position was isolated from the mixture by Sephadex G-50 spin-column chromatography, and collected in 100 µl of 10 mM phosphate buffer containing 100 mM NaCl and 1 mM EDTA, pH 7.5. One hundred microliter of 0.5 M ethylenediamine (pH 7.7) was added to the solution containing 5'-imidazolide ODN. The reaction was carried out for 1 h at 50° C. The ODN was then isolated by Sephadex G-50 spun-column chromatography. The conjugation of 5'-ethylenediamine-ODN to PEG was performed by adding NHS-derivatized PEG. The stoichiometric molar ratio (ODN/PEG) of the conjugation reaction was 1:5. The reaction mixture was incubated for 3 h at room temperature and dialyzed against deionized water to remove unreacted PEG (MWCO 3500). Thereafter, the product from each reaction step was analyzed by an HPLC system equipped with UV detector. The chromatography was performed on Hipore RP304 column (250×4.6 mm, Biorad, Hercules, Calif.) with detection at 260 nm using a linear gradient elution of 100 mM ammonium acetate/acetonitrile from 5/95 (v/v) to 50/50 (v/v) with a flow rate of 1 ml/min. The eluate was monitored by UV absorption measurement at 260 nm.

Figure 3:
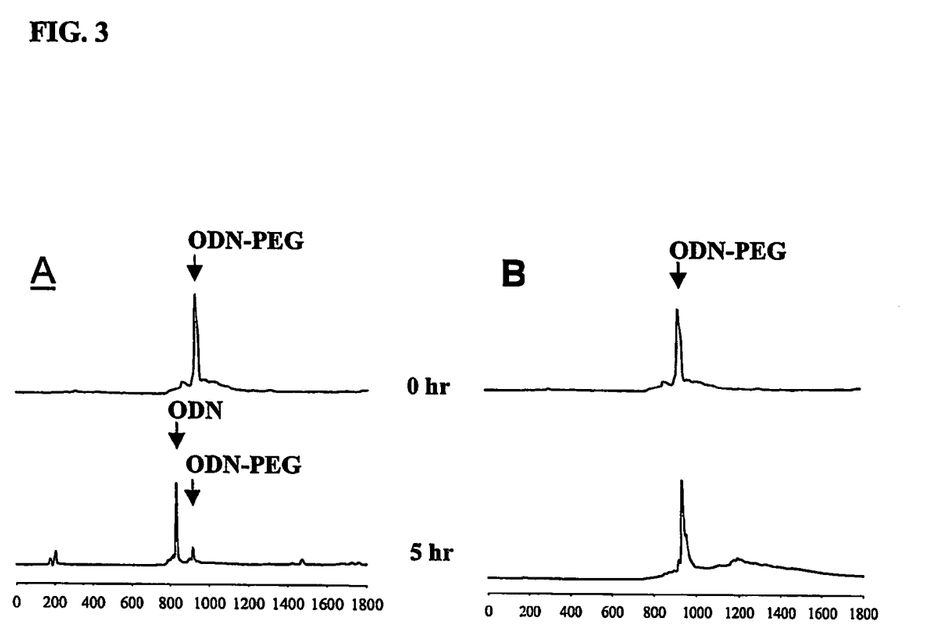
FIG. 3 is reversed-phase HPLC chromatograms showing results of analyzing cleavage profiles of ODN-PEG conjugate at pH 4.7 (A) and pH 7.4 (B), according to an example of the present invention.
Figure 4:
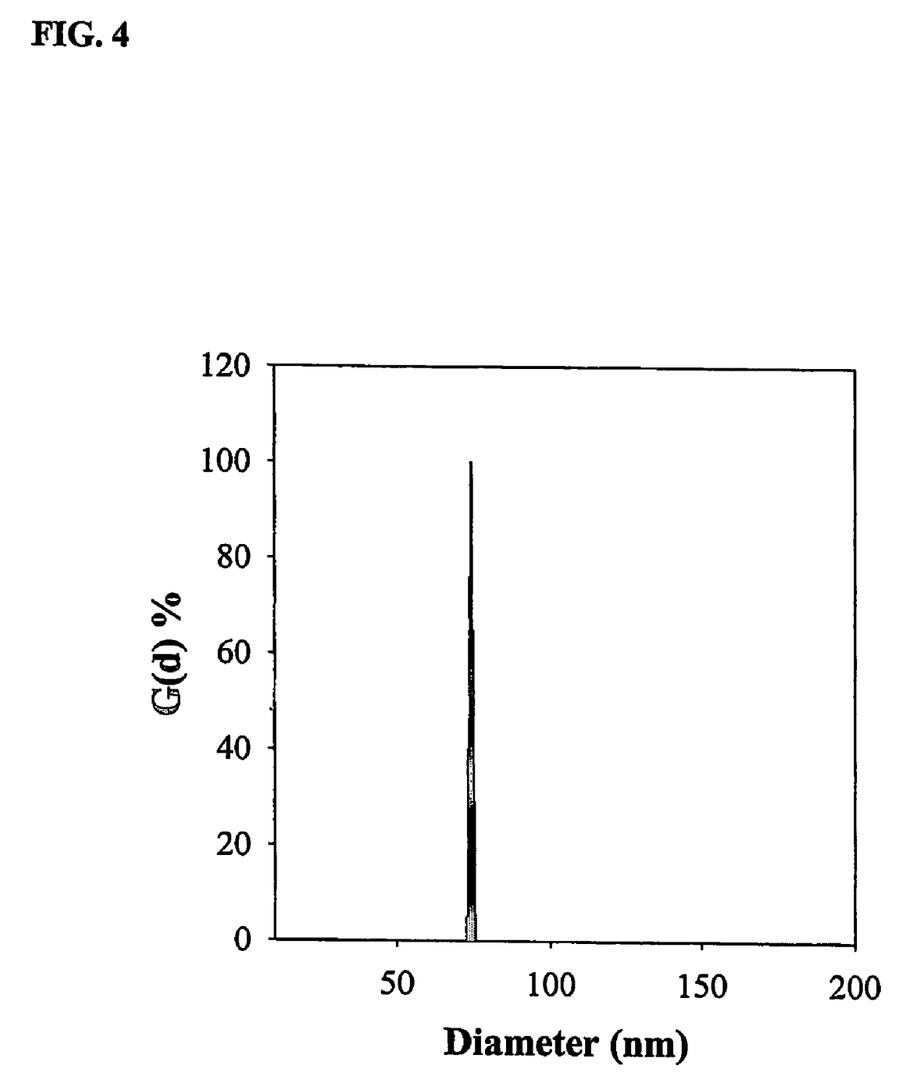
FIG. 4 is a graph showing the size distribution of ODN-PEG/KALA polyelectrolyte complex micelles as determined by dynamic light scattering, according to an example of the present invention.

Then, the synthesized conjugate having acid-cleavable bonds was evaluated for dissociation of the oligonucleotide under an acidic condition, and the results are given in FIG. 3. To observe the acid-cleavage profile of ODN-PEG conjugate, the samples were incubated at either pH 4.7 (10 mM citric acid/sodium citrate buffer, pH 4.7) or pH 7.4 (10 mM phosphate buffer, pH 7.4). The samples were incubated at 37° C. After 5 h, the sample incubated in pH 4.7 was neutralized by adding 0.1 N NaOH then injected to the HPLC system for analysis. Free ODN was also analyzed in the same HPLC system to identify its retention time.

EXAMPLE 2

Synthesis of Oligonucleotide-PEG Conjugate Having Non-Cleavable Linkage

To conjugate an oligonucleotide with polyethylene glycol (PEG) by non-cleavable linkage, an oligonucleotide having an amine group (—NH$_2$) at its 5' end was employed. First, after dissolving 1 mg (179 nmol) of the oligonucleotide having amine group (—NH$_2$) at its 5' end in 400 µl of 5 mM phosphate buffer (pH 7.4), this oligonucleotide solution was slowly added to 100 µl of a solution of methoxy-PEG activated by N-hydroxysuccinimide (methoxy-PEG-NHS, MW 2000, dissolved in 5 mM phosphate buffer (pH 7.4)), followed by incubation with agitation for 3 hr, resulting in production of an oligonucleotide-PEG conjugate, where the two components were conjugated by formation of a non-cleavable carbamate bond. The unreacted PEG was removed by dialysis against deionized water (MWCO 5000).

EXAMPLE 3

Formation of Oligonucleotide-PEG/KALA Polyelectrolyte Complex Micelle and its Characterization To obtain a gene transfer vehicle capable of transferring the oligonucleotide-PEG conjugate synthesized and isolated in Example 1 to target cells, polyelectrolyte complex micelles were prepared using a cationic peptide, such as KALA or protamine, or a cationic polymer, such as polyethylenimine. Herein, formation of polyelectrolyte complex micelles using KALA is suggested as an example with detailed description, as follows. First, the oligonucleotide-PEG conjugate was diluted in an equal volume of PBS, and KALA dissolved in PBS was then added to the diluted conjugate to form polyelectrolyte complex micelles, followed by incubation at room temperature for 30 min to stabilize the formed micelles, wherein the ratio of positive charge of the KALA peptide to negative charge of the oligonucleotide was 1:1 (+/−=1/1).

The resulting oligonucleotide-PEG/KALA polyelectrolyte complex micelles were analyzed for micellar size in an aqueous solution by dynamic light scattering (DLS). As a result, the oligonucleotide-PEG/KALA polyelectrolyte complex micelles were found to have a very narrow size distribution with a size of about 70 nm.

EXAMPLE 4

Evaluation for Intracellular Oligonucleotide Delivery Efficiency of Oligonucleotide-PEG/KALA Polyelectrolyte Complex Micelle After labeling a sense c-myb oligonucleotide complementary to the antisense c-myb oligonucleotide with a fluorescent dye, the antisense c-myb oligonucleotide-PEG conjugate prepared in Example 1 was hybridized with the labeled sense c-myb oligonucleotide. Then, a cationic peptide, KALA was added to the reaction mixture to form polyelectrolyte complex micelles. When treating cells with the formed micelles, the oligonucleotide was found to be delivered to the inside of the cells.

Figure 5A:
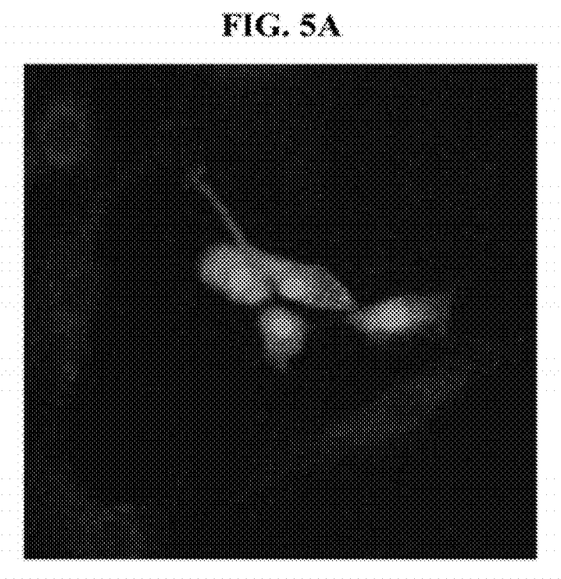
FIGS. 5A and 5B are photographs showing intracellular delivery of an oligonucleotide by polyelectrolyte complex micelles formed from an acid-cleavable bond-containing oligonucleotide-PEG conjugate and the cationic peptide KALA, observed under a confocal microscope, according to an example of the present invention.
Figure 5B:
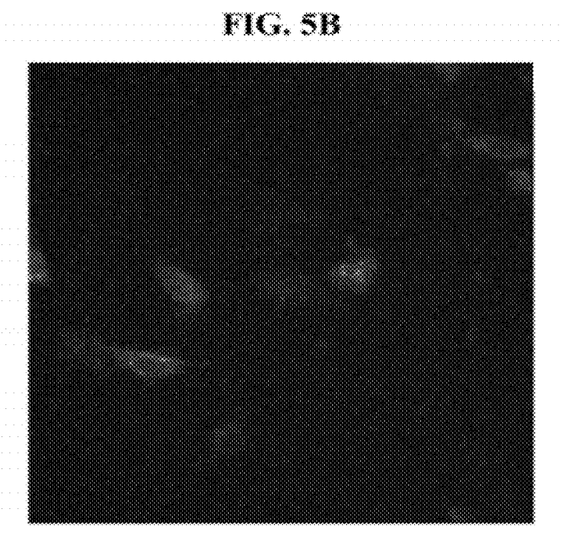

In detail, a sense c-myc oligonucleotide labeled with fluorescene isothiocyanate (FITC) at its 5' end was mixed with the oligonucleotide-PEG conjugate solution prepared in Example 1. The mixture was heated at 65° C. for 5 min and quickly cooled on ice to allow hybridization. The hybridized labeled conjugate was diluted in an equal volume of PBS, and KALA dissolved in PBS was then added to the diluted conjugate to form polyelectrolyte complex micelles, wherein the ratio of positive charge of the KALA peptide to negative charge of the oligonucleotide was 1:1 (+/−=1/1). After incubation at room temperature for 30 min, the formed polyelectrolyte complex micelles were added to the smooth muscle cell line A7R5 grown on a cover glass, followed by incubation for 3 hrs. Oligonucleotide delivery into the cells was investigated under a confocal microscope (FIG. 5A: the present invention; and 5B: a control). In detail, the A7R5 cells were aliquotted onto a 6-well plate, of which each well contained a cover glass, at a density of 5×10$^4$ cells per well, and incubated in DMEM medium containing 10% fetal bovine serum (FBS) for 24 hrs. After exchanging the culture medium with serum-free DMEM, the FITC-labeled micelles were added to the medium at a concentration of 20 µg/ml, followed by incubation at 37° C. for 3 hrs. The cells were washed with PBS four times, and fixed with 0.2% glutaraldehyde and 0.5% formaldehyde in PBS at 4° C. for 15 min. After washing with PBS, the cover glass containing cells grown thereon was transferred onto a slide glass, and then analyzed under a confocal microscope. As a result, the oligonucleotide entrapped in the oligonucleotide-PEG/KALA polyelectrolyte complex micelles was found to be delivered to the inside of the A7R5 cells. Herein, an oligonucleotide labeled with FITC but not conjugated with PEG was used as a control.

EXAMPLE 5

Figure 6:
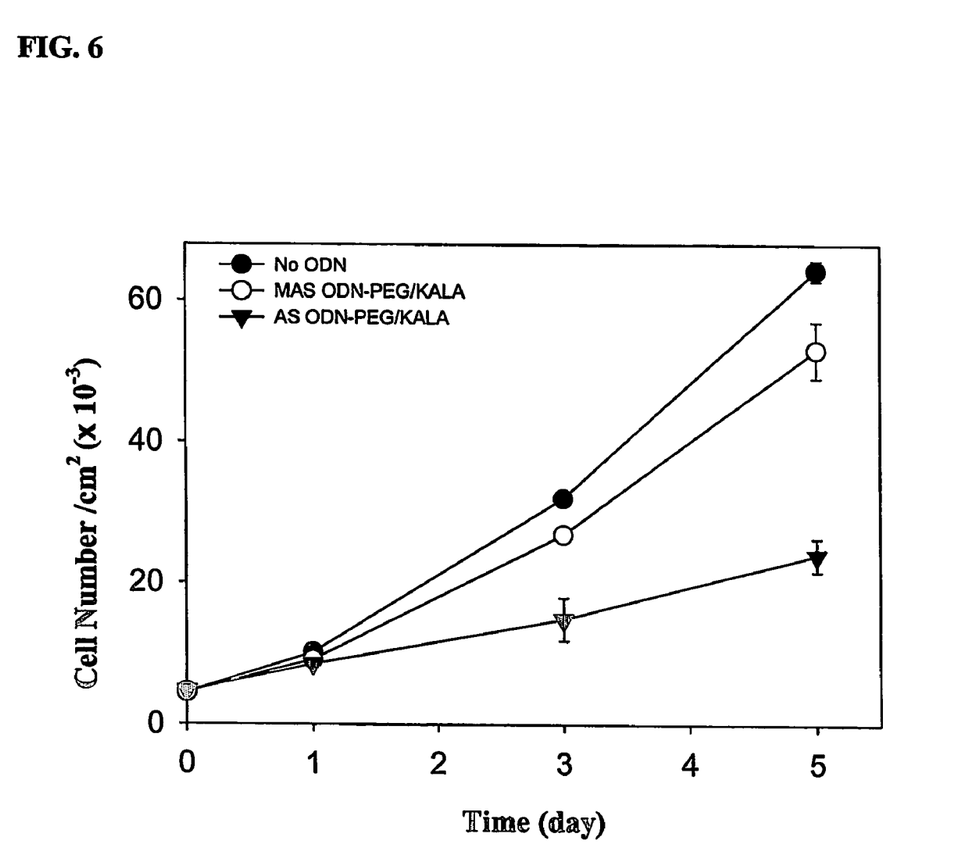
FIG. 6 is a graph showing inhibitory effect of polyelectrolyte complex micelles on proliferation rate of smooth muscle cells, where the micelles are formed from an acid-degradable bond-containing antisense c-myc oligonucleotide-PEG conjugate and the cationic peptide KALA, and such micelle formation is driven by interaction between the two components, according to an example of the present invention.
Figure 7:
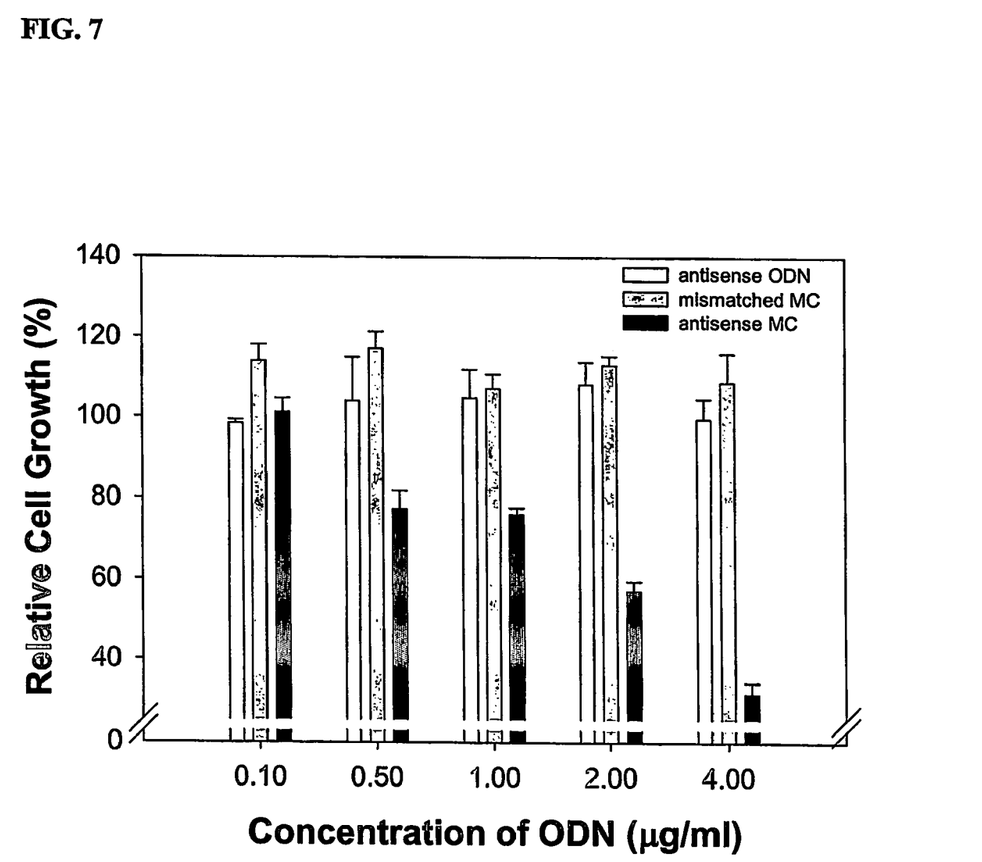
FIG. 7 is a graph showing inhibitory effect of polyelectrolyte complex micelles on proliferation of ovarian cells, where the micelles are formed from a oligonucleotide-PEG conjugate containing antisense c-raf oligonucleotide and the cationic peptide KALA, and such micelle formation is driven by interaction between the two components, according to an example of the present invention.

Evaluation for Inhibitory Effect of Antisense c-myb Oligonucleotide-PEG/KALA Polyelectrolyte Complex Micelles on Proliferation of A7R5 Smooth Muscle Cells The antisense c-myb oligonucleotide-PEG/KALA polyelectrolyte complex micelle was evaluated for inhibitory effect on proliferation of the A7R5 smooth muscle cell line, by a method of determining viable cell number, [$^3$H]thymidine uptake assay, and MTT assay measuring metabolic activity of viable cells. Herein, especially, evaluation for proliferation of cells by either counting the number of viable cells or measuring metabolic activity of the cells (MTT assay) is suggested with detailed description, as follows. Cells were seeded at a density of 4000 cells per cm$^2$ in DMEM supplemented with 10% FBS. After 24 h, the medium was replaced with a medium with 0.5% FBS. The cells were maintained in the medium containing 0.5% FBS for 48 h (Day 0). The cells were then supplemented with a medium with 10% FBS alone or with indicated amount of ODN formulations. For direct cell counting, the cells were trypsinized and counted by trypan blue exclusion on hemocytometer at appropriate time point. Degree of cell proliferation was also determined by using MTT assay after additional 72 h culture. The results are given in FIG. 6. As shown in FIG. 6, the antisense c-myb oligonucleotide-PEG/KALA polyelectrolyte complex micelles were found to have higher inhibitory activity against proliferation of the A7R5 cells than the mismatched oligonucleotide-containing polyelectrolyte complex micelles ( : antisense c-myb oligonucleotide-PEG/KALA polyelectrolyte complex micelles; : mismatched oligonucleotide-containing polyelectrolyte complex micelles; and no treatment).

EXAMPLE 6

Figure 8:
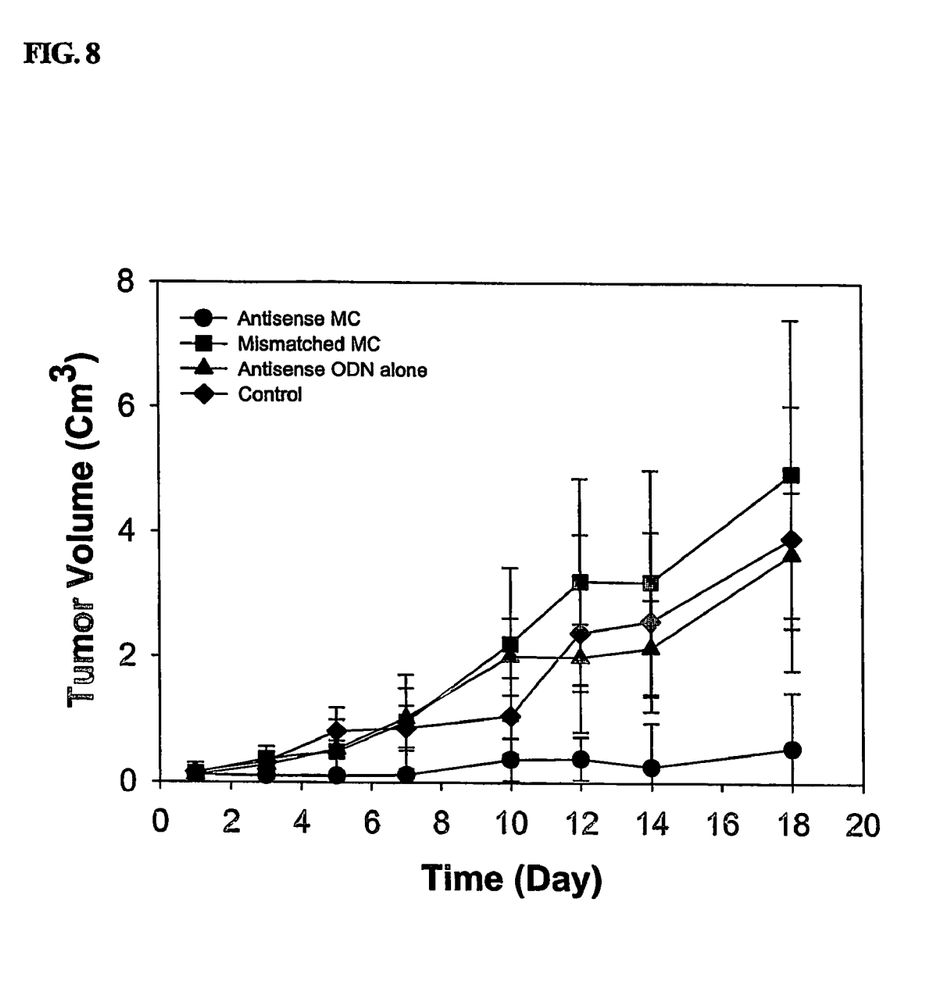
FIG. 8 is a graph showing inhibitory effect of ODN-PEG/PEI polyelectrolyte complex micelles containing antisense c-raf ODN on the growth of A2780 tumors in nude mice (n=6). Tumors were allowed to grow until a mean volume of tumor reached 0.1 cm$^3$ before treatment. Each ODN formulation was administered intratumorally at 2.5 mg kg$^{-1}$ injections$^{-1}$. The ODN formulations were injected at day 1, 3, 5, 7, 10, 12, and 14. Significant difference (P<0.05, Student's t-test) in tumor regression was observed between ODN-PEG/PEI polyelectrolyte complex micelles containing antisense c-raf ODN ( ) and antisense ODN alone ( ).

Evaluation for Inhibitory Effect of Antisense c-raf Oligonucleotide-PEG/PEI Polyelectrolyte Complex Micelles on Proliferation of Human Ovarian Cells (A2780) In Vivo Female nude mice (nu/nu) were used when 7-8 weeks old. A2780 cells (5×10$^6$ cells) were injected subcutaneously into the right flank of the mice. The administration of ODN formulations was initiated when a mean volume of tumor reached 0.1 cm$^3$. The ODN formulations in PBS were administered intratumorally at 2.5 mg kg$^{-1}$ injection$^{-1}$ at predetermined time intervals. Tumor volumes were monitored three times a week by measuring perpendicular diameters, and calculated by the following formula: length×width$^2$×π/6 (32). Statistical analysis was performed using a Student's t-test to evaluate the differences in tumor volumes. Statistical significance was defined as P<0.05. As shown in FIG. 8, the antisense c-raf oligonucleotide-PEG/polyethylenimine polyelectrolyte complex micelles were found to have higher inhibitory activity against proliferation of the A2780 cells than the mismatched oligonucleotide-containing polyelectrolyte complex micelles and antisense oligonucleotide alone ( : antisense c-raf oligonucleotide-PEG/KALA polyelectrolyte complex micelles; : mismatched oligonucleotide-containing polyelectrolyte complex micelles; : antisense c-raf oligonucleotide alone and : no treatment).

INDUSTRIAL APPLICABILITY

As described hereinbefore, the conjugate according to the present invention interacts with a cationic peptide or cationic polymer, resulting in formation of polyelectrolyte complex micelles, and the polyelectrolyte complex micelles can effectively transfer an oligonucleotide as a therapeutic agent into cells, making it possible to obtain desired activity of the oligonucleotide in target cells even when the micelles are clinically applied at a relatively low concentration. Therefore, the conjugate is very useful in basic life science research and the medical field.

The invention claimed is:

1. A conjugate for gene transfer, consisting of an oligonucleotide intended to be transferred into a target cell and a hydrophilic polymer, wherein an end of the oligonucleotide is covalently linked to the hydrophilic polymer via an acetal bond.

2. The conjugate as set forth in claim 1, wherein the hydrophilic polymer is selected from non-ionic polymers having a molecular weight of over 500 daltons.

3. The conjugate as set forth in claim 1, wherein the oligonucleotide has a molecular weight ranging from 1,000 to 50,000 daltons.

4. The conjugate as set forth in claim 1, wherein the hydrophilic polymer is one or more selected from the group consisting of polyethylene glycol, polyvinylpyrrolidone and polyoxazoline.

5. The conjugate as set forth in claim 1, wherein monomers of the oligonucleotide are linearly linked via a phosphodiester bond.

6. The conjugate as set forth in claim 1, wherein the oligonucleotide is an antisense oligonucleotide.

7. The conjugate as set forth in claim 6, wherein the antisense oligonucleotide comprises a nucleotide sequence complementary to a portion or entire nucleotide sequence of c-myc gene.

8. The conjugate as set forth in claim 1, wherein the conjugate is synthesized by the steps comprising activating an end of an oligonucleotide, and covalently linking a biodegradable hydrophilic polymer to the end of the oligonucleotide.

9. The conjugate as set forth in claim 8, wherein a chemical compound activating a functional group at the end of the oligonucleotide is selected from 1-ethyl-3,3-dimethylaminopropyl carbodiimide (EDAC), imidazole, N-hydroxysuccinimide (NHS) and dicyclohexylcarbodiimide (DCC), HOBt (1-hydroxybenzotriazole), ρ-nitrophenylchloroformate, carbonyldiimidazole (CDI), and N,N'-disuccinimidylcarbonate (DSC).

10. A polyelectrolyte complex micelle formed from the conjugate for gene transfer of any one of claims 1 to 7 and a cationic polymer or cationic peptide, wherein formation of the micelle is driven by ionic interaction.

11. The polyelectrolyte complex micelle as set forth in claim 10, wherein cationic peptide is KALA or protamine.

12. The polyelectrolyte complex micelle as set forth in claim 10, wherein cationic polymer is one or more selected from polyethylenimine, polyamidoamine, polylysine, diethylaminoethyldextran, polydimethylamino-ethyl methylacrylate, and derivates thereof.

13. A method of preparing a polyelectrolyte complex micelle, comprising inducing ionic interaction between the conjugate for gene transfer of any one of claims 1 to 7 and a cationic polymer or cationic peptide.

* * * * *